US006620093B2

(12) United States Patent
Waldmann et al.

(10) Patent No.: US 6,620,093 B2
(45) Date of Patent: Sep. 16, 2003

(54) DEVICE FOR PRE-OPERATIVE DEMONSTRATION OF IMPLANTABLE HEARING SYSTEMS

(75) Inventors: Bernd Waldmann, Basel (CH); Hans Leysieffer, Taufkirchen (DE)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 09/989,059

(22) Filed: Nov. 21, 2001

(65) Prior Publication Data

US 2002/0062059 A1 May 23, 2002

(30) Foreign Application Priority Data

Nov. 21, 2000 (DE) ........................................ 100 57 584

(51) Int. Cl.[7] .......................... H04R 25/00; A61B 5/00; A61B 5/12

(52) U.S. Cl. ............................ 600/25; 600/559; 73/585

(58) Field of Search ..................... 600/25, 559; 330/10; 381/318, 320

(56) References Cited

U.S. PATENT DOCUMENTS 4,680,798 A * 7/1987 Neumann ................... 381/320
5,719,528 A * 2/1998 Rasmussen et al. .......... 330/10
5,833,626 A * 11/1998 Leysieffer ................... 600/559
6,113,531 A * 9/2000 Leysieffer et al. ............ 600/25
6,128,392 A * 10/2000 Leysieffer et al. .......... 381/318

* cited by examiner

*Primary Examiner*—Eric F. Winakur
*Assistant Examiner*—Nikita R Veniaminov
(74) *Attorney, Agent, or Firm*—Nixon Peabody LLP; David S. Safran

(57) ABSTRACT

In order to substantially realistically pre-operatively demonstrate to patients having an impaired hearing the effect and sound impression of an least partially implantable hearing system including a first electronic audio signal processing unit, a demonstration device is provided which comprises an electromechanical transducer adapted for being non-invasively coupled from the side of the external auditory canal to at least approximately the center of the tympanic membrane and thus to the end point of the manubrium mallei for producing mechanical vibrations of the tympanic membrane, an electronic audio signal generator unit, and a second electronic audio signal processing unit connected between the audio signal generator unit and the electromechanical transducer for driving the electromechanical transducer, wherein the second audio signal processing unit corresponds to or simulates the first electronic audio signal processing unit. A further aspect of the invention is a process for preoperatively demonstrating the effect and sound impression of an at least partially implantable hearing system intended to be implanted.

48 Claims, 7 Drawing Sheets

DEVICE FOR PRE-OPERATIVE DEMONSTRATION OF IMPLANTABLE HEARING SYSTEMS

BACKGROUND OF THE INVENTION

1. Field of the Invention

The present invention in general relates to a device and to a method for pre-operatively demonstrating at least partially implantable hearing systems for the rehabilitation of hearing disorders. More particularly, the present invention relates to a device for pre-operatively demonstrating an at least partially implantable hearing system for the rehabilitation of hearing disorders, which device includes an electromechanical transducer adapted for being non-invasively coupled from the side of the external auditory canal to at least approximately the center of the tympanic membrane and thus to the end point of the manubrium mallei for producing mechanical vibrations of the tympanic membrane, and an electronic audio signal generator unit. The present invention further is concerned with a method for pre-operatively demonstrating an at least partially implantable hearing system, which system includes an audio signal processing unit and an electromechanical transducer which is driven by the audio signal processing unit and is adapted for being coupled to a preselected coupling site, particularly to the ossicular chain, for causing mechanical vibrations of the coupling site.

2. Description of Related Art

In addition to rehabilitation of congenitally deaf persons and those who have lost their hearing using cochlear implants, for some time, there have been approaches to offer better rehabilitation than with conventional hearing aids to patients with a sensorineural hearing disorder which cannot be surgically corrected, by using partially or totally implantable hearing aids. In most embodiments the principle consists in stimulating, via a mechanical or hydromechanical stimulus, an ossicle of the middle ear or directly the inner ear, rather than via an amplified acoustic signal of a conventional hearing aid in which the amplified acoustic signal is supplied to the external auditory canal. The actuator stimulus of these electromechanical systems is accomplished by different physical transducer principles, such as, for example, by electromagnetic and piezoelectric systems. The advantage of these processes is seen mainly in the sound quality which is improved as compared to conventional hearing aids, and, in the case of totally implanted systems, in the fact that the hearing prosthesis is not visible. Such partially and fully implantable electromechanical hearing aids are described, for example, by Yanigahara et al. (Arch Otolaryngol Head Neck, Surg, Vol. 113, August 1987, pp. 869872); Hoke, M. (ed), (Advances in Audiology, Vol. 4, Karger Basel, 1988); H. P. Zenner et al. (HNO 1998, Vol. 46, pp. 844–852; H. Leysieffer et al. ("A totally implantable hearing device for the treatment of sensorineural hearing loss: TICA LZ 3001", in HNO Vol. 46, 1998, pp. 853–863); and H. P. Zenner et al. ("Totally implantable hearing device for sensorineural hearing loss", The Lancet, Vol. 352, November 1998, No. 9142, page 1751), as well as in numerous patent documents, among others in U.S. Pat. Nos. 5,360,388; 5,772,575; 5,814,095 and 5,984,859.

Recently, such partially and fully implantable electromechanical hearing aids for the rehabilitation of internal ear damages have been introduced into clinical use. In this connection it turned out to be desirable to demonstrate to the patient to be provided with the implant the improvement of hearing or the sound quality, respectively, to be expected. The known audiological methods which until now merely provide for a stimulation of the hearing by sound transmission through the air or through the human body, do not permit such a demonstration without surgical intervention.

There are approaches for testing the middle ear by direct contact with an electromechanical transducer. In conformity with Zoellner (A. Thullen, "Clinical experiences with the sound probe according to Zoellner", Medizinal-Markt, Vol. 4, No. 12, December 1956, pages 444 and 445) a sound probe is contacted with the middle ear, particularly invasively during middle ear operations. A device for electromechanical testing of hearing (U.S. Pat. No. 5,833,626) and a device for positioning and fixing of therapeutic, surgical, or diagnostic instruments (U.S. Pat. No. 5,776,144) have been proposed for the pre-operative demonstration of implantable hearing systems and for the psychoacoustical measurement of the auditory threshold in quiet by direct mechanical stimulation of the umbo. Hofmann et al. (German Patent No. 198 21 602) propose a vibration measuring head for evaluation of the movability of the middle ear. The basic embodiment includes a transducer, particularly an electromagnetic transducer, which exclusively is operated in resonance, wherein the movability of vibratorily movable elements of the middle ear structure coupled to the actoric side of the transducer can be evaluated by means of a second measuring coil, because the dampening of the system by the middle ear structure coupled thereto is represented by a variation of the voltage generated by this coil.

In the meantime, the device suggested in U.S. Pat. Nos. 5,776,144 and 5,833,626 was used for clinical examination of test persons having normal hearing. The examination showed in a statistically significant manner that this method is well reproducible and valid, and can be applied without any risk for the safety of the test persons.

However, basically there is the problem, that when using the device and the method for patients with impaired hearing, there is an individually varying audition. The differences particularly reside in spectrally very different courses of the auditory threshold in quiet as well as possibly in a positive recruitment (increase of the steepness of the soundness perception) and a reduced frequency resolution power for above-threshold signals. The known devices and methods scarcely permit successes because an individual compensation of the respective hearing disorder, i.e. an adaptation of the electronic audio signal processing unit driving the electromechanical transducer in the sense of an adaptation of a hearing aid, can not be carried out. This necessarily results in the serious disadvantage of the proposed devices and methods that the pre-operative demonstration never provides the patient with the hearing impression he will encounter later on after implantation and individual adaptation of the implanted hearing system to his individual hearing impairment.

SUMMARY OF THE INVENTION

The primary object of the present invention is to devise a device and a method for pre-operatively demonstrating at least partially implantable hearing systems, which permit a non-invasive testing of the hearing capacity as it will be encountered after implantation and adaptation of an individual hearing system.

In accordance with one aspect of the invention this object is achieved by a demonstration device for pre-operatively demonstrating an at least partially implantable hearing system for the rehabilitation of hearing disorders, said hearing system including an electronic audio signal processing unit, said device comprising:

an electromechanical transducer adapted for being non-invasively coupled from the side of the external auditory canal to at least approximately the center of the tympanic membrane and thus to the end point of the manubrium mallei for producing mechanical vibrations of the tympanic membrane, an electronic audio signal generator unit, and an electronic audio signal processing unit connected between the audio signal generator unit and the electromechanical transducer for driving the electromechanical transducer, wherein the audio signal processing unit of the demonstration device corresponds to or simulates the electronic audio signal processing unit of the hearing system intended to be implanted.

By the demonstration device of the present invention the action and the sound impression to be expected upon implantation of the respective hearing system can be demonstrated in a very realistic manner to the patient having a hearing disorder.

Preferably, means are provided for adapting the audio signal processing unit of the demonstration device to the individual hearing disorder of the respective patient.

Furthermore, means for playing back a data carrier or a sound carrier are preferably associated to the audio signal generator unit. In this connection all types of signals may be utilized which usually are used for audiological purposes, such as pure sinusoidal sounds, narrow-band noise, wide-band noise, speech, music and so on. Also all known embodiments of data carriers and means for generating these test signals may be used, such as an analog and/or digital generation or synthesizing, an analog or digital storage in all known types of non-rewritable or rewritable analog and/or digital storage media, such as semiconductor storages, analog sound carriers (e.g. magnetic tape), audio CDs, CD-ROMs and so on.

In conformity with the invention means for storing a plurality of parameter sets for setting the audio signal processing unit of the demonstration device, and means for selecting and transmitting to the audio signal processing unit of the demonstration device any one of said plurality of parameter sets may be provided. In such an embodiment of the demonstration device of the invention different "standard" parameter sets for setting the audio signal processing unit of the demonstration device, in which sets the individual parameters are adapted to each other in an advantageous manner, may be determined and stored in advance. The operator of the demonstration device then can select any one or any combination of the stored parameter sets without an individual setting of individual parameters being required. Furthermore, no deepened knowledge of the effects of individual parameters or of the interaction of pluralities of parameters is necessary in order to attain more or less optimum parameter settings, so that the demonstration device then also can be properly operated by less trained personal.

The audio signal processing unit of the demonstration device preferably comprises a programmable processor unit, particularly a personal computer (PC) or a digital signal processor (DSP). The presently used term "personal computer" or "PC" is to be understood as also including notebooks, laptops and the like, as well as any other "external" computers, i.e. computers which are independent of the transducer driver.

The programmable processor unit may be configured for carrying out the functions of audio signal generator unit as well as of the audio signal processing unit of the demonstration device.

In conformity with a particularly preferred embodiment of the invention the audio signal processing unit of the demonstration device comprises electronic driver means for driving the electromechanical transducer, wherein a digital-to-analog converter may be connected between the programmable processor unit and the electronic driver means. Particularly, when using as the programmable processor unit a personal computer which carries out the functions of the audio signal generator unit as well as of the audio signal processing unit of the demonstration device, the electronic driver means and the digital-to-analog converter may be integrated in a hardware interface which is connected between the personal computer and the transducer.

When, however, the programmable processor unit is a digital signal processor (DSP), a particularly compact demonstration device may be obtained by integrating the electronic driver means, the digital-to-analog converter and the digital signal processor in a hardware interface. In order to simplify the operation of this hardware interface, furthermore display means may be provided for displaying audio signal generation data and audio signal processing data. The display means likewise may be integrated in the hardware interface or may be connected to the latter.

The audio signal processing unit of the demonstration device preferably comprises electronic audio signal processing means and electronic driver means for driving the electromechanical transducer, which are at least approximately the same as electronic audio signal processing means and electronic driver means included in the hearing system intended to be implanted, and which may be integrated in an interface.

In order to attain an impression of the output-side deflection of the transducer which is independent from individual variations of the biological load impedance, the electromechanical transducer preferably has a mechanical source impedance which, in the entire spectral transmission range of the device, is distinctively higher than the mechanical load impedance defined by the biological system comprising tympanic membrane, ossicular chain and inner ear.

The examination may be carried out in a manner which is particularly comfortable to the patient, when the electromechanical transducer comprises a transducer housing which provides for an acoustical encasing that minimizes sound signals emitted by vibrating structures of the transducer to such an extent that an acoustical deafening of the contralateral, non-examined ear becomes unnecessary.

The electromechanical transducer may be based on the electrodynamic, electromagnetic, magnetostrictive, capacitive or piezoelectric transducer principle. Particularly preferred is a piezoelectric transducer because magnetic stray fields may be completely avoided thereby.

In conformity with a further embodiment of the invention, a coupling element may be provided which is adapted to be coupled to the electromechanical transducer and to be non-invasively contacted, through the external auditory canal, with at least approximately the center of the tympanic membrane and thus the end point of the manubrium mallei. Preferably, this coupling element is a rod-shaped member which is stiff in axial direction thereof and which has an actuator end remote from the transducer, which actuator end is configured for a non-traumatic mechanical contact with the center of the tympanic membrane. Advantageously, the rod-shaped coupling element is configured such that it can be easily manually flexed to adapt it to the individual geometrical configuration of the external auditory canal.

Preferably, the electromechanical transducer is disposed within a transducer housing configured for introduction into an inlet zone of the external auditory canal, wherein the transducer housing has geometrical dimensions which are selected such that an examining person, even when using a microscope, has an unobstructed view of the actuator end of the coupling element contacting the center of the tympanic membrane. This permits the examining person to easily introduce the device, while at the same time providing for the safety of the patient.

Furthermore, by connecting the coupling element to the transducer via mechanical plug-type connection means, rather than by a mechanically fixed connection, different coupling elements may be used, which elements may be easily exchanged e.g. for hygienic reasons and which may be configured as disposable articles.

Preferably, the electromechanical transducer, possibly in combination with the mechanical coupling element, has a first mechanical resonance frequency at the upper end of the spectral transmission range of ≧10 kHz. A broadband behavior and thus short transient times may be attained thereby.

In conformity with a further embodiment of the invention, positioning means are provided for positioning the electromechanical transducer with respect to the umbo. Thereby the transducer, or, when the latter is coupled to the coupling site by a mechanical coupling element, such as a coupling rod connected to the electromechanical transducer, the actor end of the coupling element may be precisely moved to the target point.

Fixing means are preferably provided to obtain a secure, play-free linkage of the positioning means to a human skull and thus to fix the relative spatial positions of the positioned transducer or the coupling element, respectively.

In conformity with a further preferred embodiment of the invention, an intermediate element is provided between the positioning means and the electromechanical transducer, wherein this intermediate element is configured and dimensioned to transmit quasi-steady-state positioning adjustments from the positioning means to the electromechanical transducer, but to sufficiently reduce the transmission of at least dynamic forces from the positioning means to the coupling element to such an extent that the risk of middle or inner ear damage is substantially reduced.

In the demonstration device of the invention, the transducer together with the coupling element, follows the relatively slow position changes which are called quasisteady-state here and which are caused by the actuation of the positioning means. The physician can thus guide the active end of the coupling element precisely and free of relative movements to structures in the human body, especially to the umbo, as the target point. However, in the case of an unintentional external action which generally takes place by jerks and jolts, for example by hitting the positioning means with the hand, an instrument or the like, the dynamic forces acting on the positioning means are kept away from the transducer and the coupling element at least to a substantial extent.

The intermediate element may be made as a spring member, which is a structurally simple approach. The spring member, the electromechanical transducer and the coupling element from a spring/mass system which preferably has a natural frequency in the range from 0.5 to 5 Hz.

A further aspect of the invention is a process for pre-operatively demonstrating an at least partially implantable hearing system intended to be implanted, said hearing system comprising a first audio signal processing unit having a predetermined audio signal processing behavior, and a first electromechanical transducer which is driven by said first audio signal processing unit and which is adapted for being coupled to a pre-selected coupling site for causing mechanical vibrations of the coupling site, said process comprising the steps of:

(a) providing a second audio signal processing unit having an audio signal processing behavior which at least approximates the audio signal processing behavior of said first audio signal processing unit, and supplying test and demonstration signals to the second audio signal processing unit to produce output signals for driving a second electromechanical transducer;

(b) storing the output signals produced in step (a) in a signal storage;

(c) repeating steps (a) and (b) with different sets of audiological adaptation parameters;

(d) non-invasively coupling the second electromechanical transducer from the side of the external auditory canal to at least approximately the center of the tympanic membrane and thus to the end point of the manubrium mallei; and (e) applying to the second electromechanical transducer output signals stored in the signal storage for causing mechanical vibrations of the tympanic membrane.

Accordingly, the process of the invention is carried out in two phases. In a first phase output signals of the type produced by an audio signal processing unit of the hearing system intended to be implanted are stored in a signal storage for different sets of audiological adaptation parameters. In a second phase, the actual demonstration phase, a transducer (the second electromechanical transducer) is non-invasively coupled from the outside via the external auditory canal to at least approximately the center of the tympanic membrane of the hearing-impaired patient to whom the hearing impression of the hearing system to be implanted is to be demonstrated, whereupon output signals stored in the signal storage are applied to the second transducer to mechanically vibrate the tympanic membrane. Thereby the functions of the implant can be demonstrated to a possible implant carrier in a non-invasive but nevertheless realistic manner.

Different settings of the implant may be simulated and demonstrated, respectively, by applying to the second transducer output signals obtained for different sets of audiological adaptation parameters.

The second electromechanical transducer may be coupled to at least approximately the center of the tympanic membrane directly or via a coupling element which is introduced through the external auditory canal for contacting the tympanic membrane.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
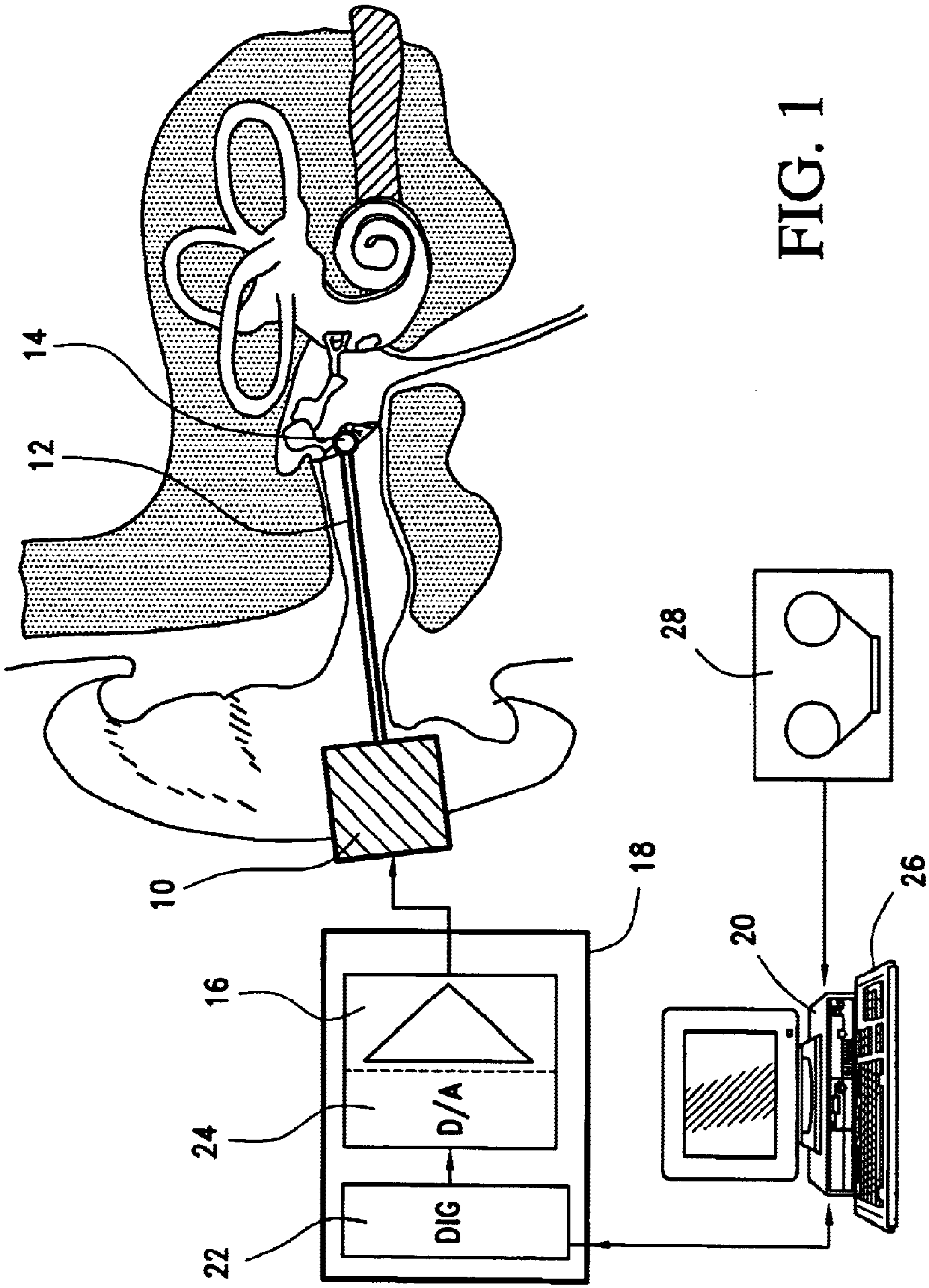
FIG. 1 shows a first embodiment of a pre-operative demonstration system in which the electronic audio signal processing means of the hearing device to be implanted are simulated by software.

The pre-operative demonstration system schematically shown in FIG. 1 comprises an electromechanical transducer 10 which outputs mechanical oscillations that are transmitted via a coupling element 12 to the center of the tympanic membrane (umbo) 14 by direct mechanical contact. The associated mounting means for the transducer and their interconnection are not illustrated in FIG. 1 and will be described in detail with reference to FIGS. 5 and 6.

The transducer 10 is controlled by electronic driver means provided in a hardware interface 18. This interface is digitally controlled by a computer, for example personal computer (PC) 20, via a serial interface (for example RS 232, V.24). Interface 18 includes a digital logical unit (DIG) 22 for bi-directional data communication with the personal computer, a digital-to-analog converter 24, and a driver unit 16 which is connected to the output side of converter 24 and which is adapted to the physical principal of the electromechanical transducer 10. In this embodiment, the audio signal processing of the implant system to be demonstrated is simulated in computer 20 purely digitally based on proper software.

The audiological adaptation parameters of this simulation software for adaptation to the respective individual hearing disorder of the patient can be changed via the operating unit of the computer, typically a keyboard 26. The simulation software preferably includes a module which guides the operator, e.g. the audiologist of an examination team, in a user-friendly manner, for example in a dialogue-type process. The simulation software may operate in a true real-time mode (online) and may permit access to all possible parameters and parameter changes to be found in the respective hearing implant.

In conformity with a second alternative embodiment a plurality of parameter sets for different audiological adaptation profiles may be made available to the operator, and the operator selects among them the parameter set which is best suited for the respective individual hearing disorder. According to a third alternative embodiment the simulation of the audio signal processing of the respective implant system may be effected by transmitting test and demonstration signals over the real audio signal processing means of the respective implant system and by storing the resulting output signals in a signal storage unit. Preferably, the resulting output signals are digitized and stored on suitable digital data storage media. This process is repeated with different sets of audiological adaptation parameters. Then, these pre-processed audio data sets are available in the signal storage unit, for example a CD-Rom, offline, and they can be selected by the operator of the demonstration device in a user-guided manner.

In all the above mentioned embodiments the individual audiological adaptation to the individual hearing disorder may be carried out in communication with the patient in an interactive and iterative manner as this commonly is done in an audiological adaptation process of a conventional hearing aid. The respective patient himself also may actively engage in this adaptation process by varying parameters. The audio test signals required for the audiological adaptation are generated by the computer 20 itself, or are prepared and digitally stored in the computer, or may be transmitted to the computer from suitable data or sound carriers (for example audio-CD playback devices, magnetic tape devices and the like) via proper interfaces.

Figure 2:
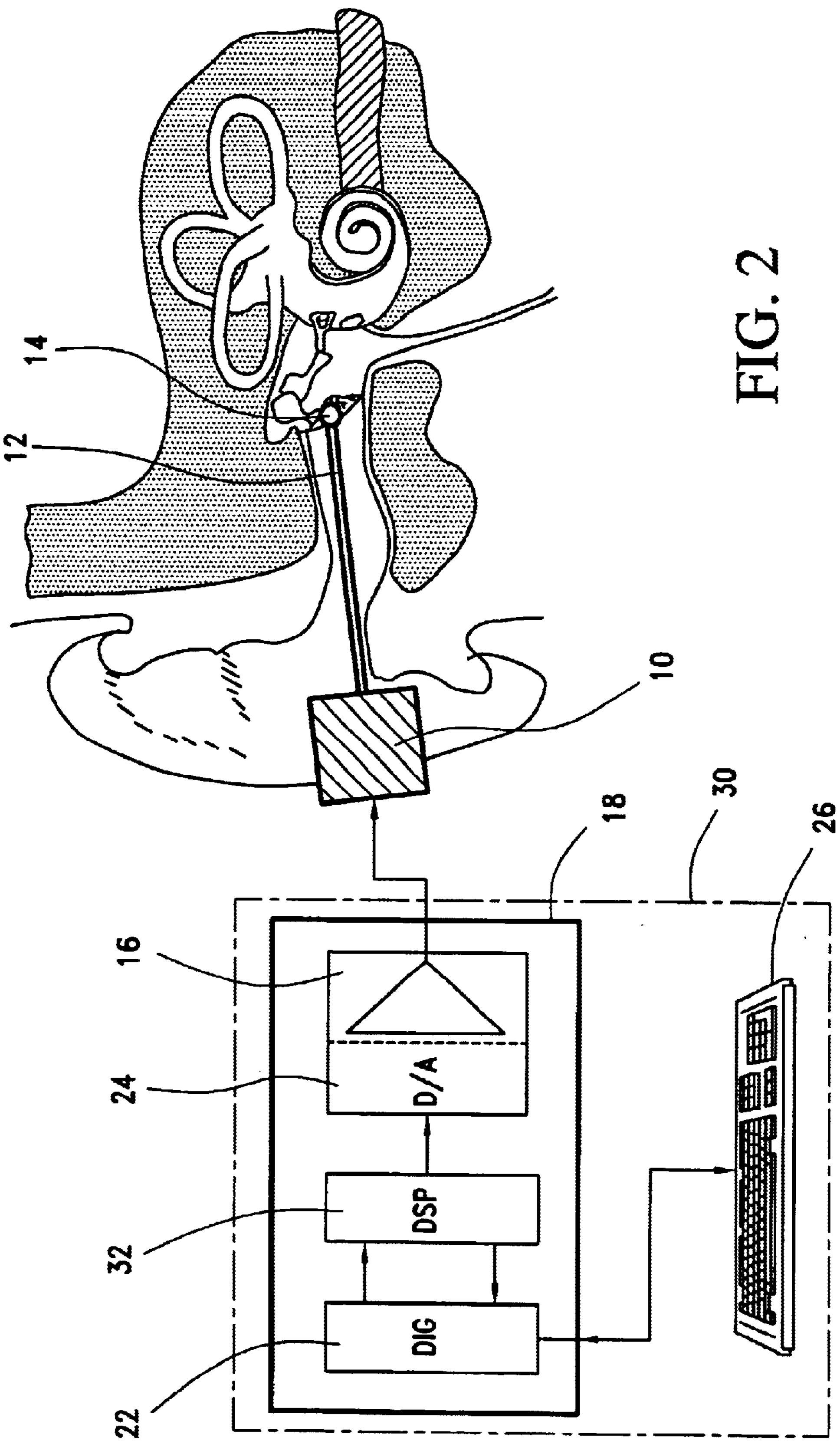
FIG. 2 shows a second embodiment of a pre-operative demonstration system similar to the system of FIG. 1.

In the embodiment schematically illustrated in FIG. 2 no external computer, such as the PC 20 shown in FIG. 1, is used; rather the above described simulations methods as well as operation and adaptation thereof are combined in a device 30 which includes an operating unit 26 (for example a keyboard) and a hardware unit 28. In this embodiment the hardware unit 28 comprises a digital signal processor (DSP) 32 which carries out all the above described simulation and audiological adaptation tasks. In a manner analog to the embodiment of FIG. 1, the device 30 includes a digital-to-analog converter 24 and a driver unit 16 by which the digital output signals generated by the signal processor 32 are converted into analog signals, are amplified and are applied to the electromechanical transducer 10.

The device 30 further comprises a digital logical unit (DIG) 22 which represents a, preferably bi-directional, data communication interface to permit transmission of adjustment parameters and data commands as well as of externally generated audio test signals from a playback device 28 to the digital signal processor 32, but also transmission of signals generated by the digital signal processor 32 to a display and/or recording device (not illustrated in FIG. 2) for facilitated operator guidance and for purposes of documentation.

Instead of simulating the operation and the signal behavior of the electronic audio signal processing means of the hearing device to be implanted, the preoperative demonstration system also may be designed such that the audio signal processing unit used to control the electromechanical transducer comprises the same audio signal processing means as provided in the hearing device to be implanted. This embodiment of the subject demonstration system is shown in FIG. 3.

In this embodiment, the entire implant electronic means 34, i.e. the audio signal processing means as well as the transducer driver means of the respective implant system (IMP), is contained, as hard- and software, in the interface 18 in the same manner as used in the respective implant system. Therefore, an online demonstration of the intended implant system with 100% identical hard- and software 34 is possible. The control of the implant hard- and software 34 and the supply of the proper audio test and demonstration signals preferably are effected via a bi-directional interface (DIG) 22 which communicates, likewise bi-directionally, with a computer 20 (for example a personal computer). The individual audiological adaptation of the system IMP to the respective hearing disorder and the generation of the audio test and demonstration signals are carried out in the same manner as described above for the embodiments of FIGS. 1 and 2.

Figure 3:
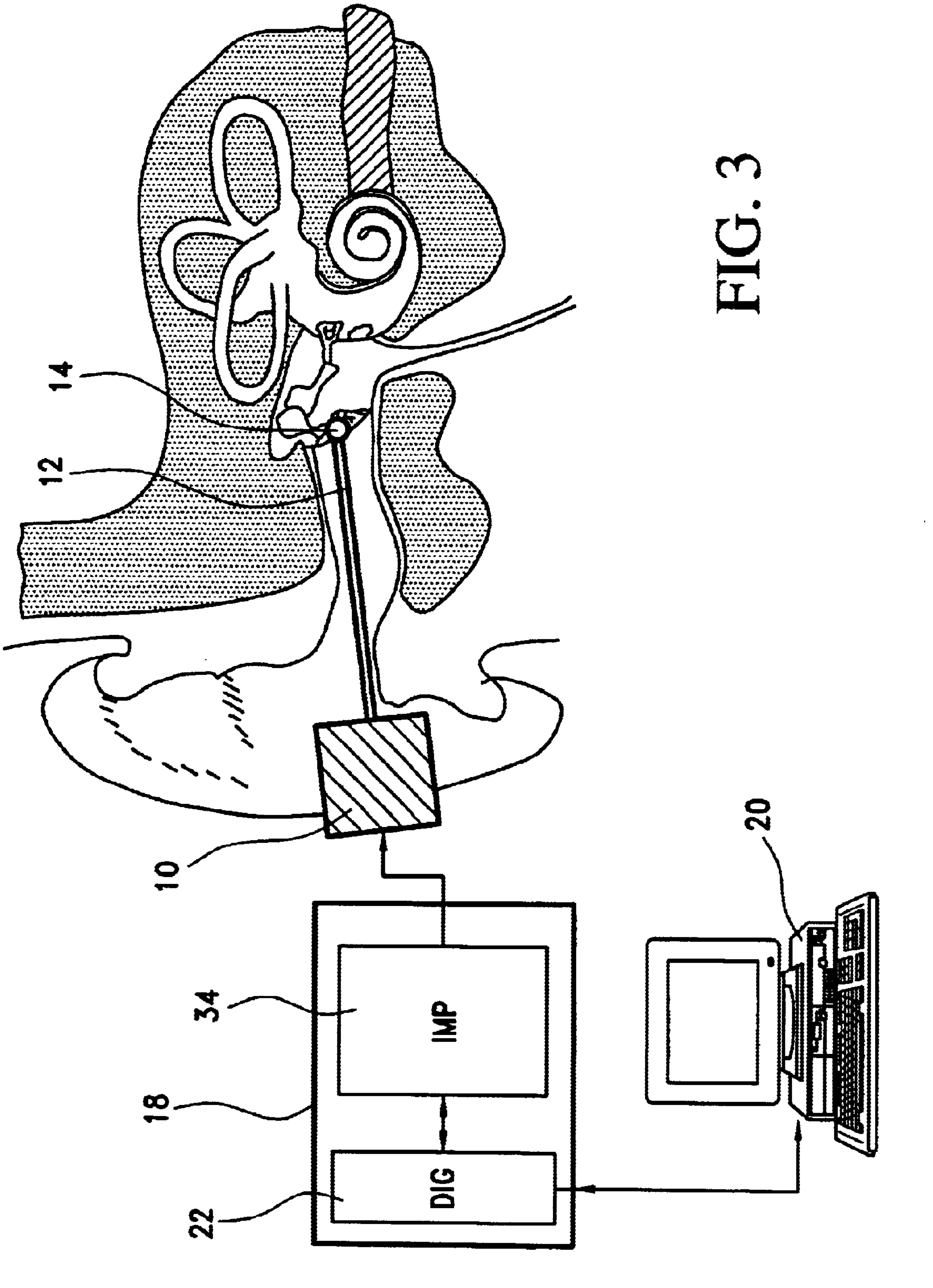
FIG. 3 shows a third embodiment of a pre-operative demonstration system in which an audio signal processing unit for controlling an electromechanical transducer comprises electronic audio signal processing means as used in the hearing device to be implanted.
Figure 4:
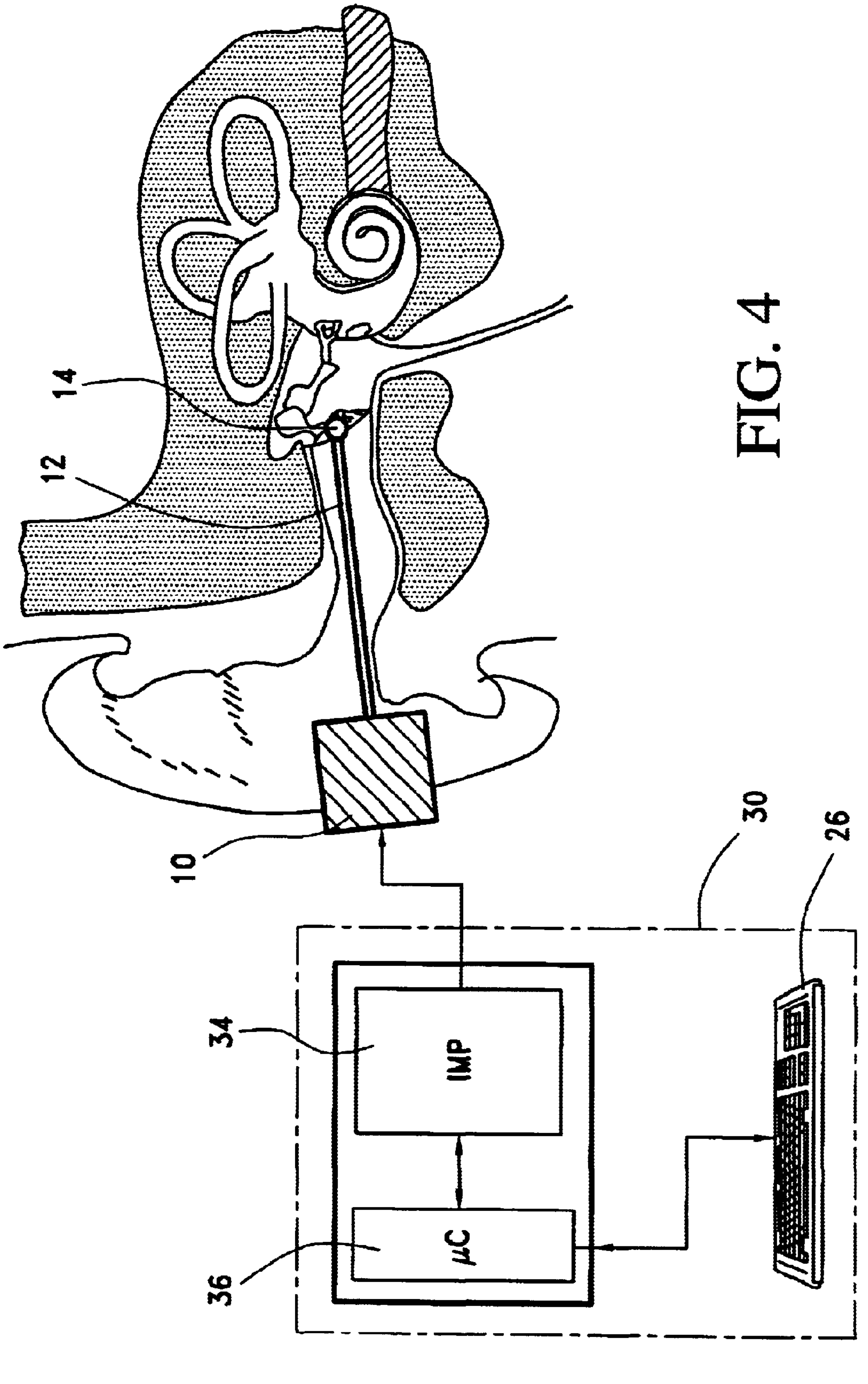
FIG. 4 shows a fourth embodiment of a pre-operative demonstration system similar to the system of FIG. 3

The further embodiment shown in FIG. 4 is similar to the embodiment of FIG. 3, but does not use an external computer (PC). Rather, the device 30 comprises, in addition to the implant system (IMP) 34, a microcontroller or microcomputer ($\mu$C) 36 which is controlled by an operating unit, for example a keyboard 26. Furthermore, a display unit (not illustrated in FIG. 4) may be provided for operator guidance. The controller ($\mu$C) 36 bi-directionally controls the system IMP. The individual audiological adaptation of the system IMP to the respective hearing disorder and the generation of the audio test and demonstration signals are carried out in the same manner as described above for the embodiments of FIGS. 1 and 2. Particularly, the provision of the audio test and demonstration signals is not illustrated in FIG. 4, but may be effected in conformity with the embodiment shown in FIG. 1.

Figure 5:
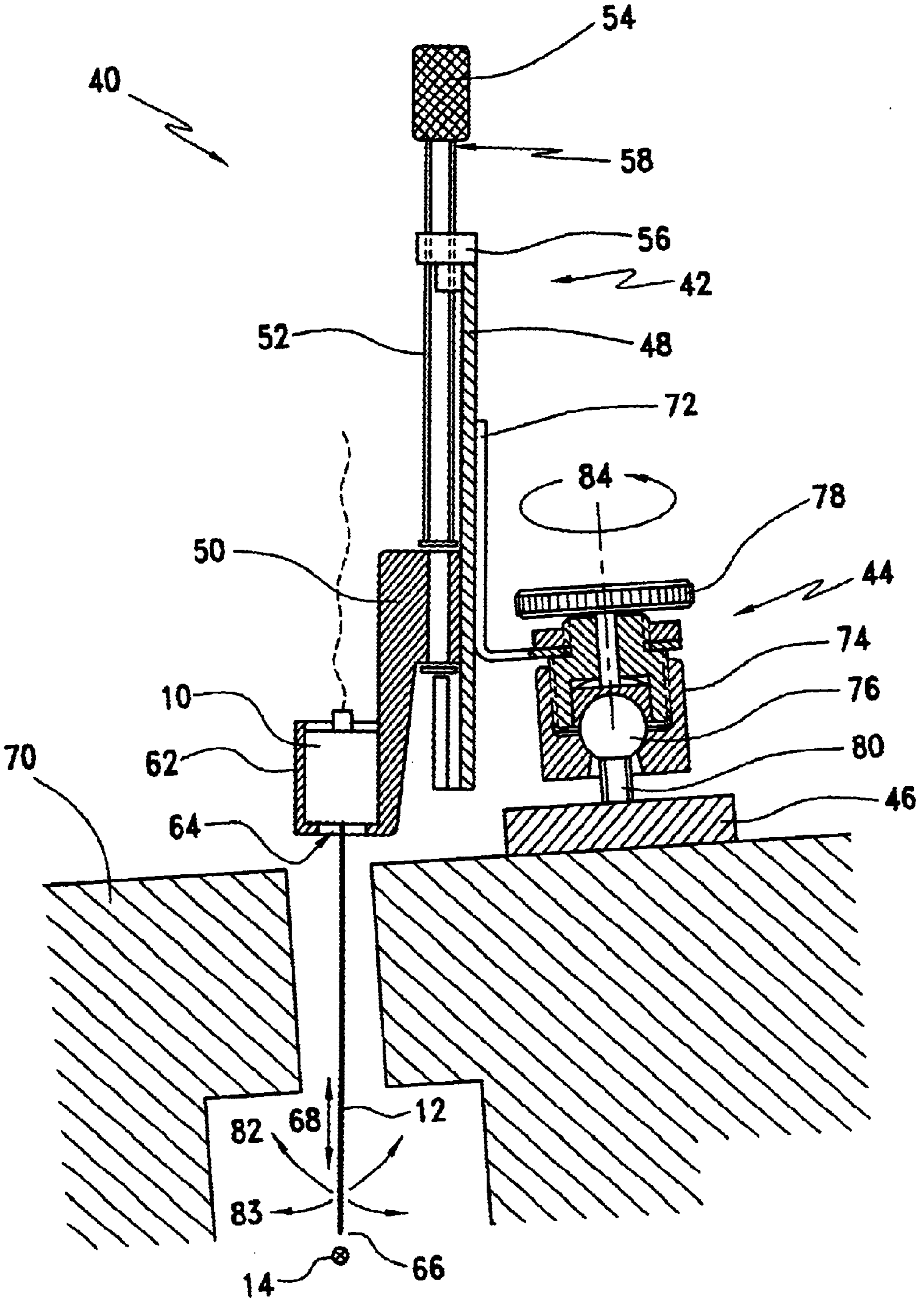
FIGS. 5 and 6 show positioning devices for positioning a coupling element of the demonstration system with respect to the umbo.

The demonstration system of the present invention preferably may be used in combination with a positioning system 40 which is shown in FIG. 5 and which is of the type described in U.S. Pat. No. 5,776,144. The positioning system 40 is composed, essentially, of a linear axis mechanism 42, a clampable ball-and-socket joint 44 and a base 46.

A carriage 50 is guided, without play, in a linear guide 48 of linear axis mechanism 42. Carriage 50 can be moved via a threaded spindle 52. A rotary knob 54 is joined securely to threaded spindle 52. The pitch of the threaded spindle 52 is designed to be self-locking, i.e. the pitch angle is smaller than the effective angle of friction, so that carriage 50 does not move automatically along linear guide 48 as a result of its weight.

The length of the path of carriage 50 moving along linear guide 48 is limited by two end stops 56, 58. The upper end stop 56 is formed by a closure plate which is provided with a corresponding internally threaded hole for receiving threaded spindle 52 and which is attached to the upper end of linear guide 48. On the one hand, the closure plate forming end stop 56 guides the threaded spindle 52 parallel to linear guide 48, and an the other hand, this plate also prevents carriage 50 from sliding off of linear guide 48 by screwing spindle 52 out too far. Similarly, the lower end stop 58, which is defined by a face at the lower end of rotary knob 54, prevents threaded spindle 52 from being screwed in too far, and thus, carriage 50 from sliding out at the opposite end of linear guide 48.

By turning rotary knob 54, according to the direction of the thread and the selected pitch of threaded spindle 52, axial displacement of the carriage 50 along guide 48 of linear axis mechanism 42 is effected. Carriage 50 can, thus, be moved continuously along the linear axis mechanism 42 between the two end stops 56 and 58, and due to the self-locking of the threaded drive, maintains its instantaneous position.

Carriage 50 has a corresponding receiver 62 into which the electromechanical transducer 10 shown in FIGS. 1 to 4 can be manually inserted without play or removed therefrom. Receiver 62 for transducer 10 has an opening 64 for the coupling element 12 which is connected to transducer 10 inserted therein. The free, active end 66 of the coupling element 12 can, thus, be positioned in axial direction 68 parallel to the linear guide 48 relative to a target point 14 in and stationary with respect to body 70, when the rotary knob 54 is turned.

Linear axis mechanism 42, together with threaded spindle 52, rotary knob 54, carriage 50 and the transducer 10 inserted in receiver 62 and held there, is joined securely to housing 74 of the clampable ball-and-socket joint 44 using a connecting element 72. Ball-and-socket joint 44 has a ball 76 which is securely joined via a column 80 to base 46, and which can be clamped with reference to the housing 74 by means of a clamp screw 78.

When the ball-and-socket joint 44 is unclamped, the entire linear axis mechanism 42 can be turned in all three rotary degrees of freedom 82, 83, 84 around the center of ball 76, which is fixedly joined to the base 46.

Via base 46, positioning system 40 can be securely joined to suitable holding means. After attachment of these holding means to the body, positioning of the system attached to the holding means and subsequent clamping of clamp screw 78, exact positioning of free, active end 66 relative to a target point 14 on the body, is thus possible without play, wherein possibly risky relative movements between the body and the free active end 66 of the coupling element are prevented.

By loosening clamp screw 78 of ball-and-socket joint 44, connecting element 72 and the linear axis mechanism 42 which is attached to it, as well as transducer 10 inserted in carriage 50, together with coupling element 12 coupled thereto and its free, active end 66, can be turned around the center of ball 76 of the ball-and-socket joint 44 according to all three rotary degrees of freedom 82, 83, 84. The shown combination of clampable ball-and-socket joint 44 and linear axis mechanism 42 securely attached to it, thus enables four-axis positioning of the free, active end 66 of the selected coupling element 12 relative to any target point 14 an the body, i.e., positioning in the translatoric degree of freedom 68 and in the three rotational degrees of freedom 82, 83 and 84.

Figure 6:
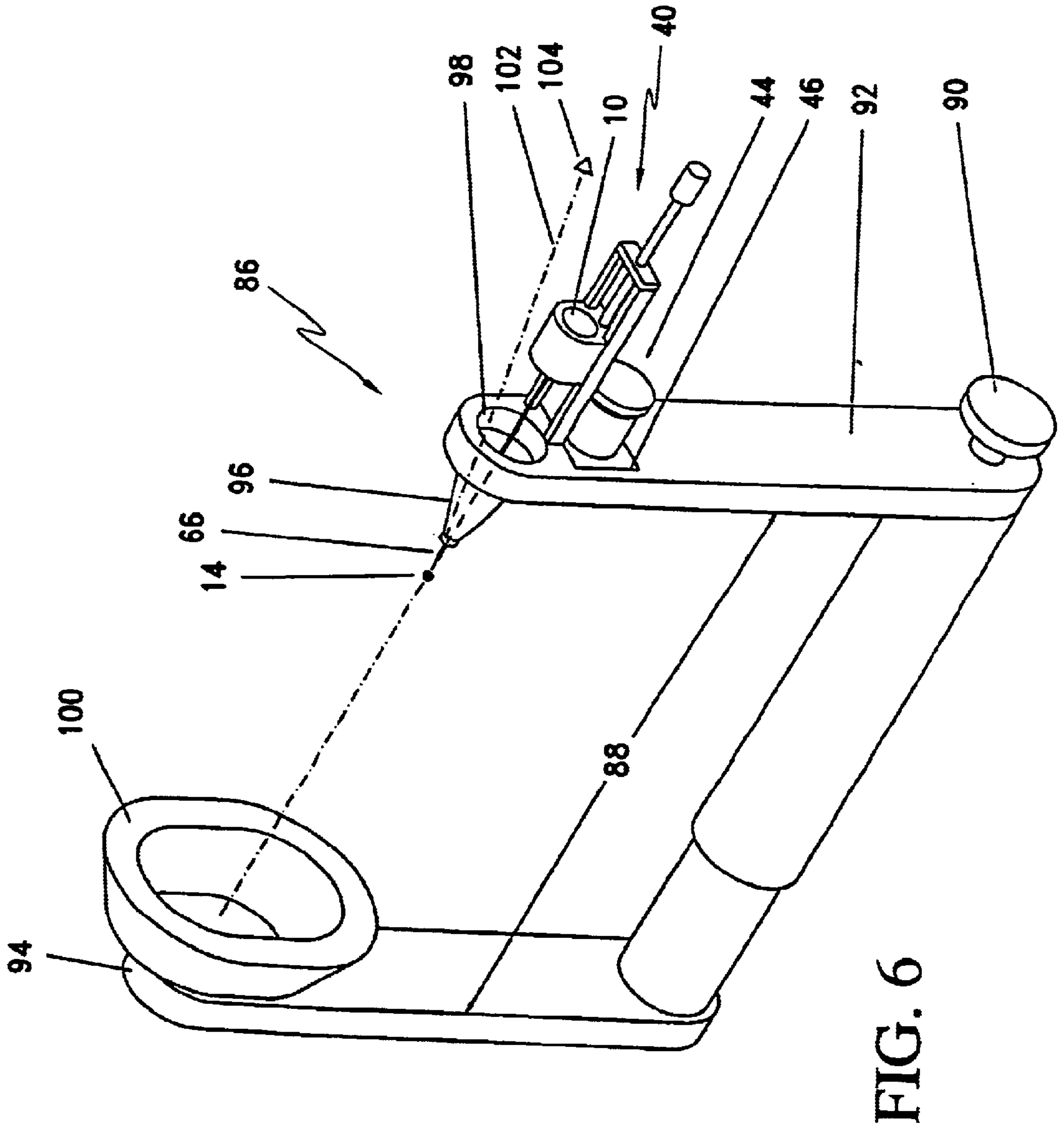

FIG. 6 illustrates a preferred combination of the positioning system 40 of FIG. 5 and a head support 86 for positioning and fixing the transducer and the coupling element, respectively, of the presently described demonstration system. In the embodiment shown here, the base 46 of the positioning system 40 is securely joined to head support 86. Opening width 88 of the head support 86 is, preferably, about 200 mm, and width 88 can be set, optionally and without play, via a rotary knob 90 and an interior threaded drive by moving a pair of receiving arms 92 and 94 towards (closing) or away (opening) from one another. Rotary knob 90 for adjustment of opening width 88, in this case, can be operated either by the wearer of head support 86 himself/herself or by a qualified specialist (physician, nurse, assistant) in order to attach head support 86 to the head of the patient by clamping on both sides. Positioning system 40, via its base 46, is securely attached to one (arm 92) of the two receiving arms. This side is called the working side of the head support. A conical retaining element 96 is connected to receiving arm 92 and can be designed, for example, similar to an ear speculum. Retaining element 96 may be cardanically mounted on receiving arm 92 to allow compensation of small spatial angles. It is inserted into the external auditory canal of the wearer (patient) with visual monitoring, if necessary, with the aid of a microscope.

Conical retaining element 96, moreover, has a conical inside opening 98 which provides space for the free, active end 66 of the coupling element 12 clamped in positioning system 40 and also for visual control. The positioning system 40 is mounted on the head support 86 in such a manner that the optical axis 102 of the microscope or of the unaided eye 104, respectively, is not covered by the positioning system 40 or components thereof.

On the receiving arm 94 at the opposite side of head support 86, selectively, a second conical support, similar to support 96, or an earmuff element 100 in the form of a half shell, is attached. The second conical support or earmuff element 100 is, respectively, inserted into the auditory canal or placed over the outer part of the opposite ear.

When earmuff element 100 is used, as is shown in FIG. 6, some of the pre-tensioning force generated by reducing the opening width 88 is transferred over a large area to the skull bone area which surrounds the outer ear. This prevents compressive forces from being applied at points and the associated undesirable feeling of pressure associated with it, and the force applied for support is distributed over a large area of skin.

After inserting conical retaining element 96 into the outer auditory canal at the working side and the subsequent placement of the earmuff element 100 on the outer ear at the opposite side, by carefully reducing opening width 88 of head support 86, the two retaining elements, i.e., retaining element 96 and earmuff element 100, can be caused to approach one another until the entire head support 86 is clamped on the skull of the patient. By deforming earmuff element 100 and by blocking conical retaining element 96 in the outer auditory canal, a secure fitting of the entire head support 86 on the skull of the patient is ensured. After clamping head support 86 on the skull of the patient, the free active end 66 of the coupling element 12, attached in positioning system 40, thus can be positioned, through conical inside hole 98 in conical retaining element 96, without play in a manner preventing relative movements between the skull and target point 14 on the skull. The set position of the positioning system can be fixed via the described clamping means of the positioning system.

Figure 7:
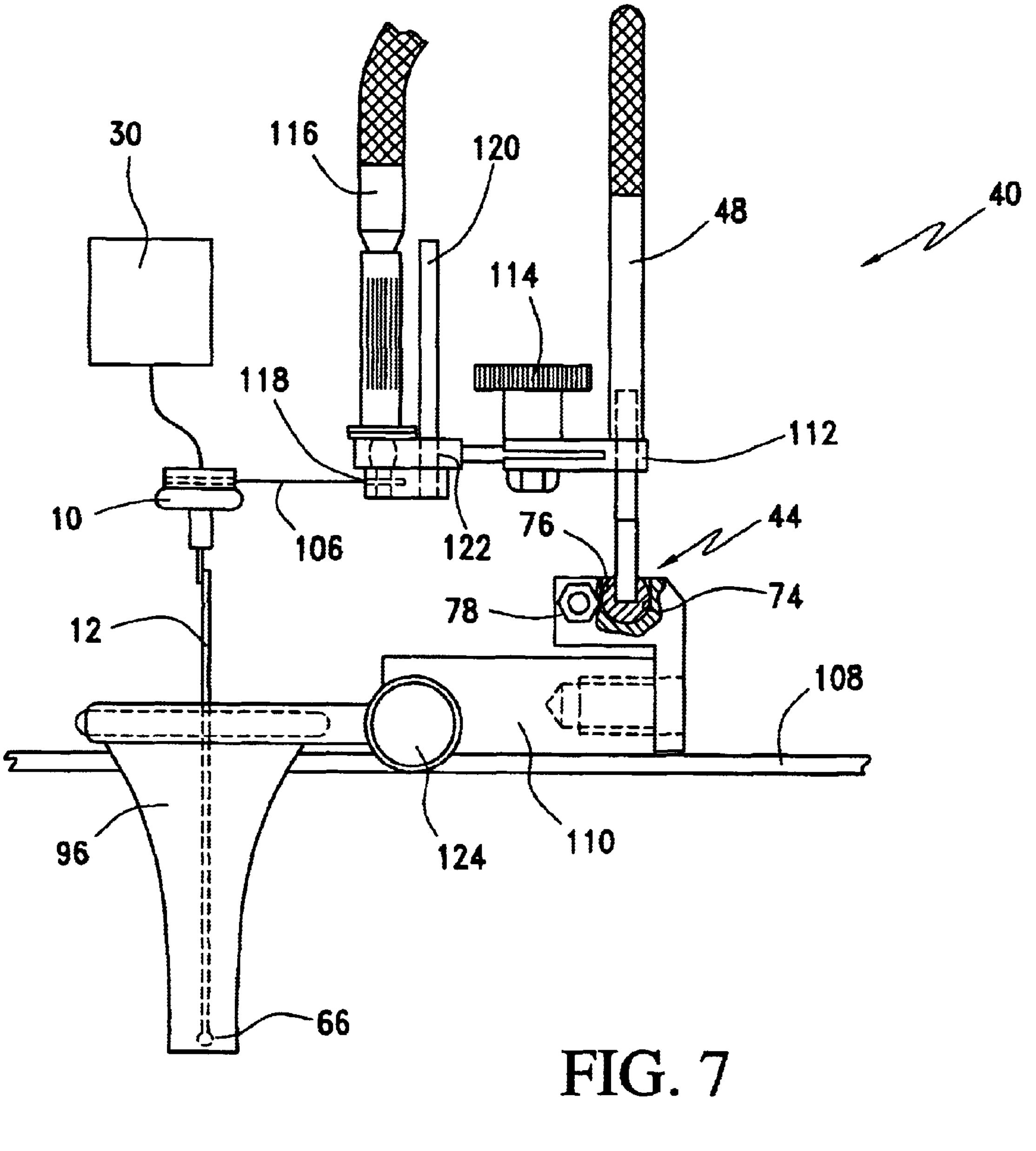
FIG. 7 shows a further embodiment of a pre-operative demonstration system in which an intermediate member is disposed between the positioning device and the transducer for attenuating the transmission of dynamic forces acting on the positioning device to the transducer.

FIG. 7 shows a further embodiment of the above described preoperative demonstration device in which the transducer 10 is connected via an intermediate element 106 to a positioning system 40. The positioning system 40 in turn is attached to a fixing means which is only schematically shown at 108 and which makes it possible to link the positioning system 40 to the human body, especially to the human skull, securely and without play. The electromechanical transducer 10, the output side of which is fixedly connected to a rigid coupling rod, is driven in a manner corresponding to that used in the embodiments of FIGS. 1 to 4.

In a manner similar to the embodiments of FIGS. 5 and 6, the positioning system 40 is provided with a base 110 which is coupled to the fixing means 108. The base 110 carries a clampable ball-and-socket joint 44 which has a ball 76 and an associated ball receiver 74. By means of a clamp screw 78, the ball joint 44 can be locked in a position which can be set by means of a linear guide 48 which is fixedly connected to the ball 76. A transversely extending support arm 112, the length of which is adjustable, is attached to the linear guide 48. The adjusted length of the support arm 112 is fixed by means of a clamping screw 114. A linear adjustment device 116 engages the end of the support arm 112 which is remote from the linear guide. This device is connected on its end which is the bottom end in the FIG. 7 to a slide 118 to which a guide pin 120 is attached. The guide pin 120 is movably guided in a hole 122 of the support arm 112 in a direction which is essentially parallel to the longitudinal axis of the coupling rod 12. The transducer 10 is connected to the slide 118 via the intermediate element 106. By means of the linear adjustment device 116 the transducer 10 can be sensitively adjusted via the slide 118 and the intermediate element 106 in the longitudinal direction of the coupling rod 12. The linear adjustment device 116 may include a hydraulic piston/cylinder arrangement which is not shown in detail and which, upon actuation on its end which is remote from the transducer 10, allows fine adjustment of the transducer 10 together with the coupling rod 12 relative to the support arm 112 in a direction which is essentially perpendicular to the latter.

Furthermore, an ear speculum 96 is attached to base 110 in an easily removable manner. To secure and release the ear speculum 96 a clamp 124 which interacts with the base 110 and the ear speculum 96 is used. The ear speculum 96 accommodates the part of the coupling rod 12 remote from the transducer 10, wherein the longitudinal axis of the coupling rod 12 can be aligned with the longitudinal axis of the ear speculum. Optionally, the ear speculum 96 can be cardanically supported on the base 110 to compensate for small spatial angles.

When the ball joint 44 is unclamped, the linear adjustment device 116 can be turned around the center of the ball 76 in all three rotational spatial degrees of freedom. The mutual distance of the longitudinal axes of the linear guide 48 and the coupling rod 12 can be adjusted when the clamping screw 114 is loosened. By attaching the fixing means 108 to the body of the test person, positioning of the system attached to the fixing means, subsequent clamping of the clamping screws 78 and 114 and corresponding adjustment of the linear adjustment device 116 is possible. Thus, exact, play-free positioning of the free actuator end 66 of the coupling rod 12 relative to the umbo as the target point on the body is possible, wherein the free actuator end 66 preferably is spherical. The position of the free actuator end 66 can be checked, for example, by a microscope. The mutual offset of the coupling rod 12 and the positioning means 40 ensures that the optical axis 102 of the microscope or the naked eye of the physician is not covered by the positioning system itself or by its components.

In the illustrated embodiment, the intermediate element 106 consists of two simple flexional springs arranged in parallel, of which in the figure only one can be seen, while the other extends offset normal to the plane of the figure and behind the spring to be seen. The intermediate element 106, the electromechanical transducer 10, and the coupling rod 12 form a spring/mass system which is preferably designed such that it has a natural or resonant frequency (or, in the case of several natural frequencies, a lowest first natural frequency) in the range from 0.5 to 5 Hz. In this way, dynamic forces having a frequency higher than this natural frequency (such forces can occur, for example, by accidental impacts against the positioning means 40), are transmitted, if at all, only in a substantially attenuated manner from the positioning means 40 to the coupling rod 12. The coupling rod 12, however, normally follows the quasi-steady-state positioning adjustments of the positioning means 40. If, however, the transducer 10, during positioning, inadvertently comes too close to the target point, the flexional springs which form the intermediate element 106 can deflect and in this way, also counteract damage to the middle and/or inner ear.

The intermediate element 106 may basically also be constructed in a different manner. For example, the intermediate element 106 may comprise a force limiter, for example in the form of a friction or induction coupling, which allows transmission of forces only up to a predetermined upper limit.

While several embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

We claim:

1. A demonstration device for pre-operatively demonstrating an at least partially implantable hearing system for the rehabilitation of hearing disorders, said hearing system including an electronic audio signal processing unit, said device comprising:

an electromechanical transducer adapted for being non-invasively coupled from the side of the external auditory canal to at least approximately the center of the tympanic membrane and thus to the end point of the manubrium mallei for producing mechanical vibrations of the tympanic membrane, an electronic audio signal generator unit, an electronic audio signal processing unit connected between the audio signal generator unit and the electromechanical transducer for driving the electromechanical transducer, wherein the audio signal processing unit of the demonstration device corresponds to or simulates the electronic audio signal processing unit of the hearing system intended to be implanted, means for storing a plurality of parameter sets for setting the audio signal processing unit of the demonstration device, and means for selecting and transmitting to the audio signal processing unit of the demonstration device any one of said plurality of parameter sets.

2. The device as claimed in claim 1, comprising means for adapting the audio signal processing unit of the demonstration device to the individual hearing disorder of a patient.

3. The device as claimed in claim 1, wherein means for playing back at least one of a data carrier and a sound carrier are associated to the audio signal generator unit.

4. The device as claimed in claim 1, wherein the audio signal processing unit of the demonstration device comprises a programmable processor unit.

5. The device as claimed in claim 4, wherein the programmable processor unit is configured for carrying out the functions of the audio signal generator unit and of the audio signal processing unit of the demonstration device.

6. The device as claimed in claim 4, wherein the audio signal processing unit of the demonstration device comprises electronic driver means for driving the electromechanical transducer.

7. The device as claimed in claim 6, wherein the programmable processor unit is a personal computer and wherein the device further comprises a digital logical unit for data communication between the personal computer and the electronic driver means.

8. The device as claimed in claim 6, comprising a digital-to-analog converter connected between the programmable processor unit and the electronic driver means.

9. The device as claimed in claim 8, wherein the electronic driver means and the digital-to-analog converter are integrated in a hardware interface.

10. The device as claimed in claim 8, wherein the programmable processor unit is a digital signal processor and wherein the electronic driver means, the digital-toanalog converter and the digital signal processor are integrated in a hardware interface.

11. The device as claimed in claim 4, wherein the programmable processor unit is selected from the group consisting of a personal computer and a digital signal processor.

12. The device as claimed in claim 11, wherein the programmable processor unit is a digital signal processor and wherein the device further comprises display means for displaying audio signal generation data and audio signal processing data.

13. The device as claimed in claim 11, wherein the programmable processor unit is a digital signal processor and wherein the device further comprises input means for supplying commands and parameters to the digital signal processor.

14. The device as claimed in claim 1, wherein the audio signal processing unit of the demonstration device comprises electronic audio signal processing means and electronic driver means for driving the electromechanical transducer, said electronic audio signal processing means and electronic driver means being at least approximately the same as electronic audio signal processing means and electronic driver means included in the hearing system intended to be implanted.

15. The device as claimed in claim 14, wherein the electronic audio signal processing means and the electronic driver means of the demonstration device are integrated in an interface.

16. The device as claimed in claim 14, comprising a bi-directional interface for transmitting data between the audio signal generator unit and the electronic audio signal processing means.

17. The device as claimed in claim 14, comprising a microcomputer, wherein said microcomputer, the electronic audio signal processing means and the electronic driver means are combined into a structural unit.

18. The device as claimed in claim 17, comprising input means for supplying commands and parameters to the microcomputer.

19. The device as claimed in claim 14, wherein the audio signal generator unit comprises a programmable processor unit.

20. The device as claimed in claim 19, wherein the programmable processor unit is a personal computer.

21. The device as claimed in claim 1, wherein the electromechanical transducer has a mechanical source impedance which, in the entire spectral transmission range of the device, is distinctively higher than a mechanical load impedance defined by a biological system comprising tympanic membrane, ossicular chain and inner ear.

22. The device as claimed in claim 1, wherein the electromechanical transducer comprises a transducer housing which provides for an acoustical encasing minimizing sound signals emitted by vibrating structures of the transducer to an extent such that acoustical deafening of a contralateral, non-examined ear is unnecessary.

23. The device as claimed in claim 1, wherein the electromechanical transducer is a piezoelectric transducer.

24. The device as claimed in claim 1, wherein the device is configured as a double device for permitting a simultaneous stimulation and examination of both ears of a patient.

25. The device as claimed in claim 1, comprising a coupling element which is adapted to be coupled to the electromechanical transducer and to be non-invasively contacted, through the external auditory canal, with at least approximately the center of the tympanic membrane and thus the end point of the manubrium mallei.

26. The device as claimed in claim 25, wherein the coupling element is connected to the transducer via mechanical plug-type connection means.

27. The device as claimed in claim 25, wherein the coupling element is a rod-shaped member which is stiff in axial direction thereof and which has an actuator end remote from the transducer, which actuator end is configured for a non-traumatic mechanical contact with the center of the tympanic membrane.

28. The device as claimed in claim 27, wherein the electromechanical transducer is disposed within a transducer housing configured for introduction into an inlet zone of the external auditory canal, wherein the transducer housing has geometrical dimensions which are selected such that an examining person, even when using a microscope, has an unobstructed view of the actuator end of the coupling element contacting the center of the tympanic membrane.

29. The device as claimed in claim 27, wherein the rod-shaped coupling element is manually flexible.

30. The device as claimed in claim 1, wherein the electromechanical transducer has a first mechanical resonance frequency at the upper end of the spectral transmission range.

31. The device as claimed in claim 1, wherein the transducer has maximum deflection amplitudes within the range from 1 to 5 micrometers within the entire audiological spectral transmission range.

32. The device as claimed in claim 1, comprising positioning means for positioning the electromechanical transducer with respect to the center of the tympanic membrane.

33. The device as claimed in claim 32, comprising fixing means for providing a secure, play-free linkage of the positioning means to a human skull.

34. The device as claimed in claim 32, wherein an intermediate element is provided between the positioning means and the electromechanical transducer, said intermediate element being configured and dimensioned for transmitting quasi-steady state positioning adjustments from the positioning means to the electromechanical transducer, and for sufficiently reducing transmission of at least dynamic forces from the positioning means to the coupling element to an extent that the risk of middle or inner ear damage is substantially reduced.

35. The device as claimed in claim 34 wherein, the intermediate element is a spring member.

36. The device as claimed in claim 35, wherein the spring member, the electromechanical transducer, and the coupling element form a spring-mass system which has a natural frequency in the range from 0.5 to 5 Hz.

37. The device as claimed in claim 35, wherein the spring member comprises at least one flexional spring.

38. The device as claimed in claim 35, wherein the coupling element is a coupling rod and the spring member is aligned at least roughly perpendicular to the longitudinal axis of the coupling rod.

39. A process for preoperatively demonstrating an at least partially implantable hearing system intended to be implanted, said hearing system comprising a first audio signal processing unit having a predetermined audio signal processing behavior, and a first electromechanical transducer which is driven by said first audio signal processing unit and which is adapted for being coupled to a preselected coupling site for causing mechanical vibrations of the coupling site, said process comprising the steps of:

(a) providing a second audio signal processing unit having an audio signal processing behavior which at least approximates the audio signal processing behavior of said first audio signal processing unit, and supplying test and demonstration signals to the second audio signal processing unit to produce output signals for driving a second electromechanical transducer;

(b) storing the output signals produced in step (a) in a signal storage;

(c) repeating steps (a) and (b) with different sets of audiological adaptation parameters;

(d) non-invasively coupling the second electromechanical transducer from the side of the external auditory canal to at least approximately the center of the tympanic membrane and thus to the end point of the manubrium mallei; and (e) applying to the second electromechanical transducer output signals stored in the signal storage for causing mechanical vibrations of the tympanic membrane.

40. The process of claim 39, wherein the output signals produced in step (a) are digitized before being stored in the signal storage in step (b).

41. The process of claim 39, wherein step (e) is repeated for a plurality of sets of audiological adaptation parameters.

42. The process of claim 39, wherein the second electromechanical transducer is coupled in step (d) by a coupling element to at least approximately the center of the tympanic membrane.

43. A demonstration device for pre-operatively demonstrating an at least partially implantable hearing system for the rehabilitation of hearing disorders, said hearing system including an electronic audio signal processing unit, said device comprising:

an electromechanical transducer adapted for being non-invasively coupled from the side of the external auditory canal to at least approximately the center of the tympanic membrane and thus to the end point of the manubrium mallei for producing mechanical vibrations of the tympanic membrane, an electronic audio signal generator unit, and an electronic audio signal processing unit which corresponds to or simulates the electronic audio signal processing unit of the hearing system intended to be implanted, the audio signal processing unit of the demonstration device comprising, a programmable processor unit and electronic driver means for driving the electromechanical transducer, and the audio signal processing unit of the demonstration device being connected between the audio signal generator unit and the electromechanical transducer for driving the electromechanical transducer.

44. A demonstration device for pre-operatively demonstrating an at least partially implantable hearing system for the rehabilitation of hearing disorders, said hearing system including an electronic audio signal processing unit, said device comprising:

an electromechanical transducer adapted for being non-invasively coupled from the side of the external auditory canal to at least approximately the center of the tympanic membrane and thus to the end point of the manubrium mallei for producing mechanical vibrations of the tympanic membrane, an electronic audio signal generator unit, an electronic audio signal processing unit which comprises a programmable digital processor and which is connected between the audio signal generator unit and the electromechanical transducer for driving the electromechanical transducer, wherein the audio signal processing unit of the demonstration device corresponds to or simulates the electronic audio signal processing unit of the hearing system intended to be implanted, and input means for supplying commands and parameters to the digital signal processor.

45. A demonstration device for pre-operatively demonstrating an at least partially implantable hearing system for the rehabilitation of hearing disorders, said hearing system including an electronic audio signal processing unit, said device comprising:

an electromechanical transducer adapted for being non-invasively coupled from the side of the external auditory canal to at least approximately the center of the tympanic membrane and thus to the end point of the manubrium mallei for producing mechanical vibrations of the tympanic membrane, an electronic audio signal generator unit, and an electronic audio signal processing unit connected between the audio signal generator unit and the electromechanical transducer for driving the electromechanical transducer, wherein the audio signal processing unit of the demonstration device corresponds to or simulates the electronic audio signal processing unit of the hearing system intended to be implanted, wherein the audio signal processing unit of the demonstration device comprises electronic audio signal processing means and electronic driver means for driving the electromechanical transducer, said electronic audio signal processing means and electronic driver means being at least approximately the same as electronic audio signal processing means and electronic driver means included in the hearing system intended to be implanted, and wherein the demonstration device further comprises a bi-directional interface for transmitting data between the audio signal generator unit and the electronic audio signal processing means.

46. A demonstration device for pre-operatively demonstrating an at least partially implantable hearing system for the rehabilitation of hearing disorders, said hearing system including an electronic audio signal processing unit, said device comprising:

an electromechanical transducer adapted for being non-invasively coupled from the side of the external auditory canal to at least approximately the center of the tympanic membrane and thus to the end point of the manubrium mallei for producing mechanical vibrations of the tympanic membrane, an electronic audio signal generator unit, an electronic audio signal processing unit connected between the audio signal generator unit and the electromechanical transducer for driving the electromechanical transducer, and a microcomputer, wherein the audio signal processing unit of the demonstration device corresponds to or simulates the electronic audio signal processing unit of the hearing system intended to be implanted, wherein the audio signal processing unit of the demonstration device comprises electronic audio signal processing means and electronic driver means for driving the electromechanical transducer, said electronic audio signal processing means and electronic driver means being at least approximately the same as electronic audio signal processing means and electronic driver means included in the hearing system intended to be implanted, and wherein the microcomputer, the electronic audio signal processing means and the electronic driver means are combined into a structural unit.

47. A demonstration device for pre-operatively demonstrating an at least partially implantable hearing system for the rehabilitation of hearing disorders, said hearing system including an electronic audio signal processing unit, said device comprising:

an electromechanical transducer adapted for being non-invasively coupled from the side of the external auditory canal to at least approximately the center of the tympanic membrane and thus to the end point of the manubrium mallei for producing mechanical vibrations of the tympanic membrane, positioning means for positioning the electromechanical transducer with respect to the center of the tympanic membrane, fixing means for providing a secure, play-free linkage of the positioning means to a human skull, an electronic audio signal generator unit, and an electronic audio signal processing unit connected between the audio signal generator unit and the electromechanical transducer for driving the electromechanical transducer, wherein the audio signal processing unit of the demonstration device corresponds to or simulates the electronic audio signal processing unit of the hearing system intended to be implanted.

48. A demonstration device for pre-operatively demonstrating an at least partially implantable hearing system for the rehabilitation of hearing disorders, said hearing system including an electronic audio signal processing unit, said device comprising:

an electromechanical transducer adapted for being non-invasively coupled from the side of the external auditory canal to at least approximately the center of the tympanic membrane and thus to the end point of the manubrium mallei for producing mechanical vibrations of the tympanic membrane, positioning means for positioning the electromechanical transducer with respect to the center of the tympanic membrane, an electronic audio signal generator unit, and an electronic audio signal processing unit connected between the audio signal generator unit and the electromechanical transducer for driving the electromechanical transducer, wherein the audio signal processing unit of the demonstration device corresponds to or simulates the electronic audio signal processing unit of the hearing system intended to be implanted, and wherein an intermediate element is provided between the positioning means and the electromechanical transducer, said intermediate element being configured and dimensioned for transmitting quasi-steady-state positioning adjustments from the positioning means to the electromechanical transducer, and for sufficiently reducing transmission of at least dynamic forces from the positioning means to the coupling element to an extent that the risk of middle or inner ear damage is substantially reduced.

* * * * *